US00PP29832P2

(12) United States Plant Patent
Wood

(10) Patent No.: US PP29,832 P2
(45) Date of Patent: Nov. 13, 2018

(54) ***HYDRANGEA* PLANT NAMED 'SMNHSDD'**

(50) Latin Name: ***Hydrangea serrata* x *macrophylla***
Varietal Denomination: SMNHSDD

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,612

(22) Filed: Nov. 30, 2017

(51) Int. Cl.
*A01H 5/00* (2018.01)

(52) U.S. Cl.
USPC ..... Plt./250
CPC ..... *A01H 5/00* (2013.01)

(58) Field of Classification Search
USPC ..... Plt./250
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Hydrangea* cultivar named 'SMNHSDD' is disclosed, characterized by a large lace-cap inflorescence, and double individual flowers. Flowers are blue in the presence of aluminum. Plants are re-blooming. The new variety is a *Hydrangea*, normally produced as an ornamental plant for containers or gardens.

2 Drawing Sheets

Latin name of the genus and species: *Hydrangea serrata* x *macrophylla*.

Variety denomination: 'SMNHSDD'.

BACKGROUND OF THE INVENTION

The new *Hydrangea* cultivar is a product of a planned breeding program conducted by the inventor, Timothy Wood, in Grand Haven, Mich. The objective of the breeding program was to produce new *Hydrangea* varieties for garden use. The crossing resulting in this new variety was made during the Summer of 2011.

The seed parent is the commercial variety *Hydrangea serrata* 'MAK20' U.S. Plant Pat. No. 24,820. The pollen parent is the unpatented *Hydrangea macrophylla* referred to as 'SMNHMTAU'. The new variety was identified as a potentially interesting selection during the Summer of 2013, at a greenhouse in Grand Haven, Mich.

Asexual reproduction of the new cultivar 'SMNHSDD' by softwood cuttings was first performed during July of 2007, at commercial greenhouse in Grand Haven, Mich. Subsequent propagation has shown that the unique features of this cultivar are stable and reproduced true to type in multiple successive generations.

SUMMARY OF THE INVENTION

The cultivar 'SMNHSDD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHSDD' These characteristics in combination distinguish 'SMNHSDD' as a new and distinct *Hydrangea* cultivar:

1. Large lace-cap inflorescence with double individual flowers.
2. Blue flower color, in the presence of aluminum.
3. Re-blooming habit.

PARENT COMPARISON

Plants of the new cultivar 'SMNHSDD' are similar to plants of seed parent in most horticultural characteristics, however, plants of the new cultivar 'SMNHSDD' differ in the following:

1. The new variety produces double individual flowers, the seed parent produces single individual flowers.
2. The new variety produces lighter blue flowers than the seed parent.

Plants of the new cultivar 'SMNHSDD' are similar to plants of pollen parent in most horticultural characteristics, however, plants of the new cultivar 'SMNHSDD' differ in the following:

1. The new variety produces double individual flowers, the pollen parent produces single individual flowers.
2. Inflorescence of the new variety is lace-cap, inflorescence of the pollen parent is mop-head.

COMMERCIAL COMPARISON

'SMNHSDD' can be compared to the patented commercial variety *Hydrangea* 'SMHMLDD' U.S. Plant Pat. No. 25,105. These varieties are similar in most horticultural characteristics; however 'SMNHSDD' differs in the following:

1. The new variety produces individual flowers which are all double, individual flowers of this comparator are almost entirely single.

2. Flower color of the new variety is blue, flower color of this comparator is lavender.

BRIEF DESCRIPTION OF THE PHOTOGRAPHS

Figure 1:
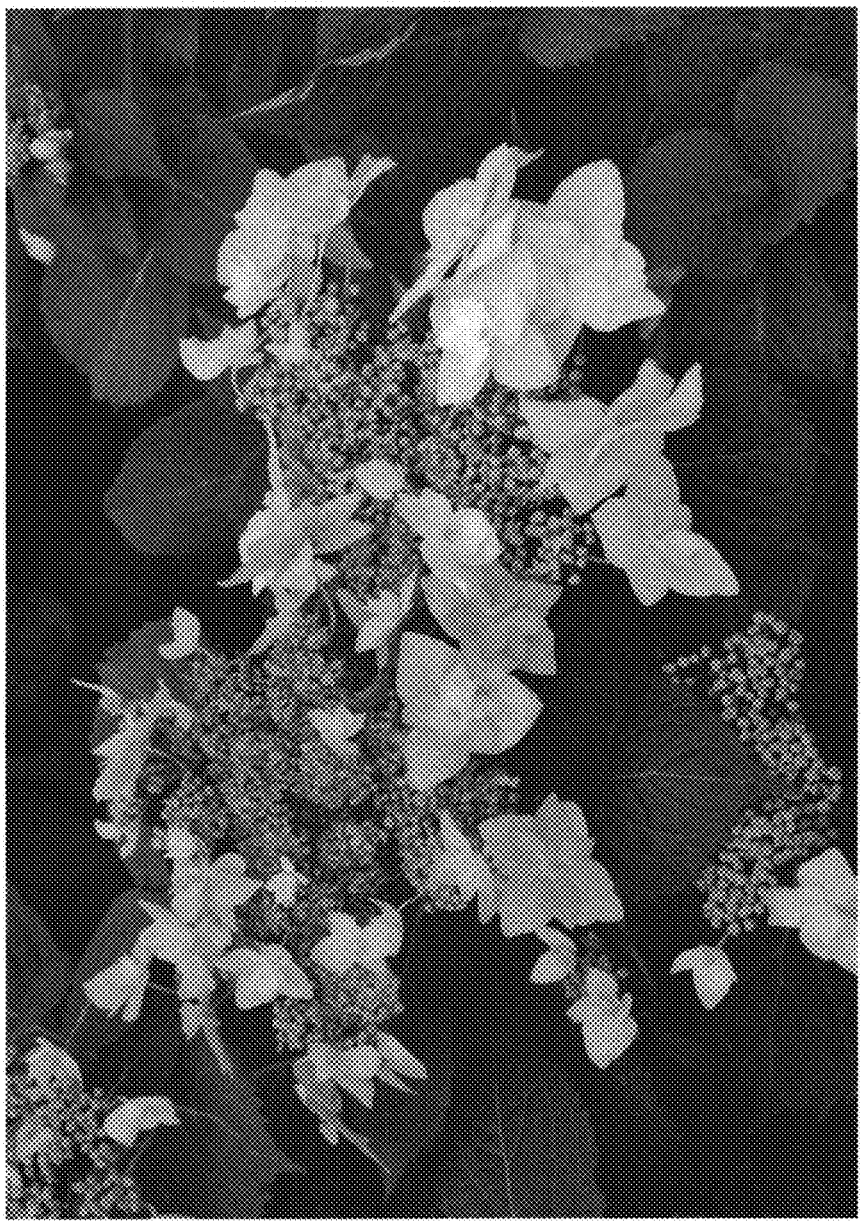

The accompanying photograph in FIG. 1 illustrates in full color typical inflorescence of 'SMNHSDD' with different nutrient treatments. The inflorescence on the left of the figure has been treated with aluminum at a lower pH. The inflorescence on the right has been grown at a high pH without aluminum. Age of the plant photographed is approximately 3 years.

Figure 2:
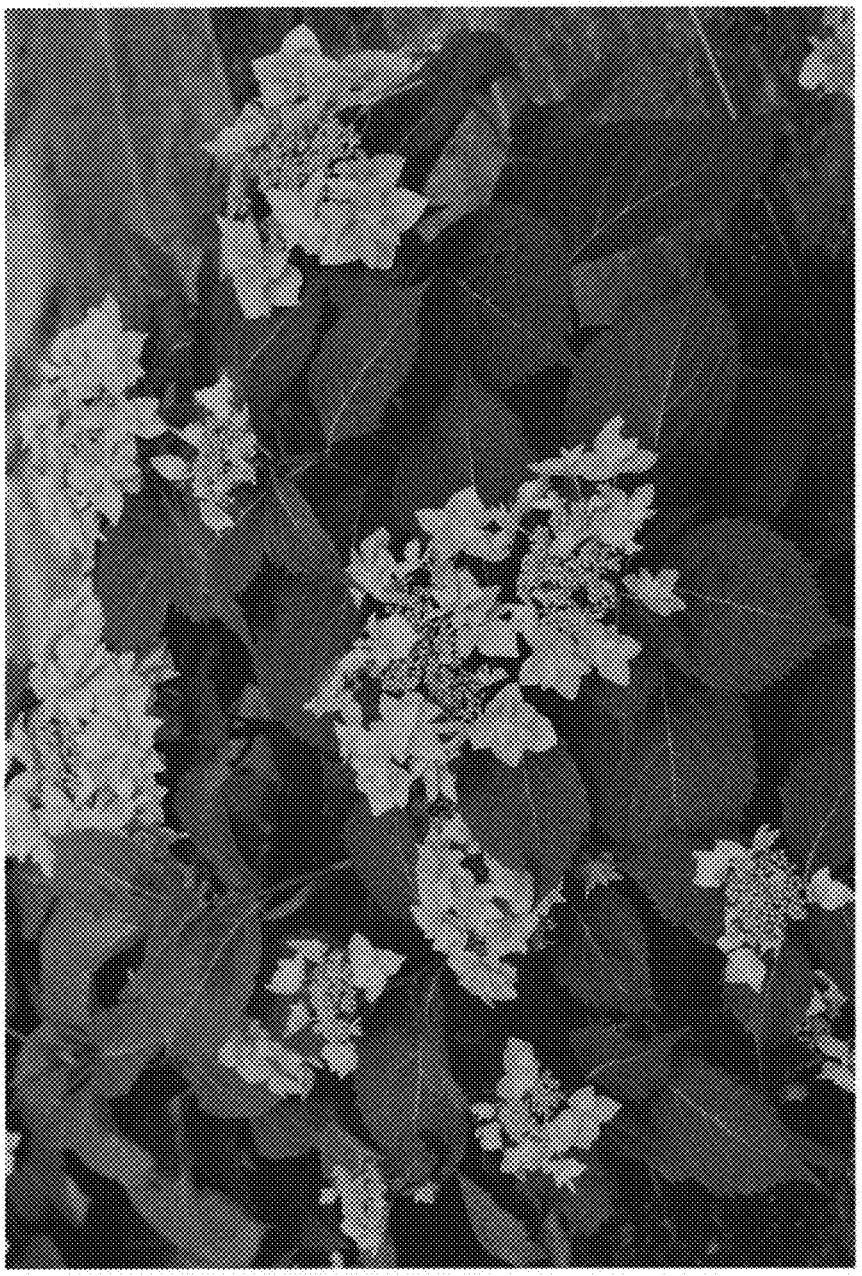

FIG. 2 illustrates typical plants of the new variety grown in a poly house in Grand Haven, Mich., treated with aluminum at approximately 2 years of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'SMNHSDD' plants grown in a poly greenhouse, in Grand Haven, Mich., USA. The growing temperature ranged from approximately 18° C. to 27° C. daytime and 5° to 10° C. at night. Measurements and numerical values represent averages of typical plant types. Measurements were taken during June of 2017.

Botanical classification: *Hydrangea serrata* x *macrophylla* 'SMNHSDD'.

PROPAGATION

Time to initiate roots: Approximately 10 days at approximately 20° C., during the Summer months.

Time to produce a rooted young plants: Approximately 30 days at approximately 20° C., during the Summer.

Root description: Both fibrous and fleshy roots present. Free to moderately free root branching, medium to thick roots. Roots mainly white, about RHS White 155D.

Propagation method: Softwood cuttings.

PLANT

Age of plant described: 2 to 3 years.
Pot size: 3 gallon.
Growth habit: Flowering perennial shrub, or sub-shrub.
Overall plant shape: Upright and mounded.
Height: 44 cm.
Plant spread: 78 cm.
Growth rate: Moderate.
Plant vigor: Good.
Branching characteristics: Upright/outward basal branches, some pinching required.
Length of lateral branches: 35 cm.
Number of lateral branches: 22.
Diameter of lateral branches: 5 mm.
Lateral branch shape: Rounded.
Lateral branch strength: Good.
Internode length: Average 2.4 cm.
Branch color: Immature: Near RHS Yellow-Green 144B. Mature: Near RHS Yellow-Green 144B.
Branch aspect: 10-45°.
Branch texture: Pubescent at upper stem, near inflorescence. Moderate quantity of lenticels. Lenticels linear to oblong, 1 to 3 mm long, colored near Greyed-Purple N187B.

FOLIAGE

Leaf:
- *Arrangement*.—Opposite.
- *Average length*.—13.5 cm.
- *Average width*.—8.7 cm.
- *Shape of blade*.—Elliptic to obovate.
- *Apex*.—Acuminate.
- *Base*.—Cuneate.
- *Margin*.—Serrate.
- *Texture and appearance of top surface*.—Rugose, leathery.
- *Texture and appearance of bottom surface*.—Leathery, prominent veins.
- *Leaf pubescence*.—Occurs on upper and lower surfaces, sparse along veins.
- *Color*.—Young foliage upper side: Near RHS Green 137A. Young foliage under side: Near RHS Green 137B. Mature foliage upper side: Near RHS Green 137A. Mature foliage under side: Near RHS Green 137B.
- *Venation*.—Type: Pinnate-arculate. Venation color upper side: Near RHS Yellow-Green 146D. Venation color under side: Near RHS Yellow-Green 146D.

Petiole:
- *Average length*.—2.2 cm.
- *Diameter*.—3 mm.
- *Color*.—Upper side: Near RHS Yellow-Green 146C.
- *Under side*.—Near RHS Yellow-Green 146C.
- *Texture upper side*.—Smooth.
- *Texture under side*.—Smooth.

FLOWER

Bloom period:
- *Natural season*.—Mid-Summer through Fall.

Inflorescence:
- *Type*.—Lace-cap.
- *Quantity of flowers per inflorescence*.—Fertile flowers: 49. Sterile Flowers: Average 11.
- *Persistent or self-cleaning*.—Persistent.
- *Fragrance*.—Mild and slightly sweet.

Panicle:
- *Shape*.—Flattened half sphere.
- *Height*.—8.9 cm.
- *Diameter*.—18.7 cm.

Sterile flower:
- *Bud shape*.—Orbicular and lobed.
- *Bud length*.—1 mm.
- *Bud diameter*.—1 mm.
- *Bud color*.—Near RHS White NN155B.
- *Flower aspect*.—Outward.
- *Flower shape*.—Irregularly round.
- *Flower length*.—Average 6.9 cm.
- *Flower diameter*.—Average 6.9 cm.
- *Flower depth*.—0.9 cm.

Sterile flower petals:
- *Petal arrangement*.—Whorled.
- *Quantity*.—6 to 7.
- *Length of petal*.—3.2 mm.
- *Width of petal*.—2.8 mm.

*Apex*.—Acute.
*Shape of petal*.—Ovate.
*Petal margin*.—Entire.
*Petal base*.—Truncate.
*Petal texture*.—Smooth, glabrous, upper and under side.
*Color*.—Upper surface at first opening: Acid: Shades of Blue, 100B, 100B and 100D, all present. Basic: Near RHS Red-Purple N74D. Under surface at first opening: Acid: Near RHS Blue 101B and 101D, both colors present. Basic: Near RHS Red-Purple N74D. Upper surface at maturity: Acid: Near RHS Blue 100B, 100B and 100D, all present. Basic: Near RHS Red-Purple N74D. Under surface at maturity: Acid: Near RHS Blue 101B and 101D, both colors present. Basic: Near RHS Red-Purple N74D. Upper surface fading to: Acidic: Near RHS Blue-Green 112B. Basic: Near RHS Red-Purple 69C. Lower surface fading to: Acidic: Near RHS Blue-Green 112A. Basic: Near RHS Red-Purple 69C.

Sterile flower sepal:
Arrangement: Double whorl
*Number*.—6 to 10.
*Shape*.—Ovate.
*Tip*.—Acute.
*Base*.—Cuneate.
*Margin*.—Irregular sub-entire dentate. Undulate.
*Length*.—Outer whorl 4.6 cm, inner whorl 2.2 cm.
*Width*.—Outer whorl — 3.2 cm; inner whorl 1.4 cm.
*Texture, upper*.—Smooth, glabrous.
*Texture, lower*.—Smooth, glabrous.
*Color*.—Upper surface at first opening: Acidic: Near Blue 101B and 101C. Basic: Close to Red-Purple 62C and 62D. Under surface at first opening: Acidic: Near Blue 101C and 101D. Basic: Close to Red-Purple 62C and 62D. Upper surface at maturity: Acidic: Near RHS Violet-Blue 98B, 98C and 98D. Basic: Close to Red-Purple 62C and 62D. Under surface at maturity: Acidic: Near RHS Blue 106B, 106C and 106D. Basic: Close to Red-Purple 62C and 62D. Fading to Upper surface: Acidic: Yellow-Green 144D, Blue 100C and Greyed-Purple 185B. Basic: Red-Purple 69D. Fading to Under surface: Acidic: Yellow-Green 144D and Blue 100D. Basic: Red-Purple 69D.

Sterile flower pedicel:
*Length*.—4.2 cm.
*Diameter*.—2 mm.
*Angle*.—15-45°.
*Strength*.—Moderate to strong.
*Texture*.—Irregular verrucate.
*Color*.—Near RHS Blue 101C.

Fertile flower:
*Bud shape*.—Orbicular.
*Bud length*.—5 mm.
*Bud diameter*.—5 mm.
Bud color.—Acidic: Blue-green 115C and Yellow-Green 145C. Basic: Red Purple 68B and Yellow-Green 145C.
*Flower aspect*.—Upright and outwardly facing.
*Flower shape*.—Round, star-shaped.
*Flower diameter*.—1.0 cm.
*Flower depth*.—4.5 mm.

Fertile flower petals:
*Arrangement*.—Whorled.
*Length of petal*.—6.0 mm.
*Width of petal*.—2.5 mm.
*Apex*.—Acute.
*Shape of petal*.—Elliptic with concave aspect.
*Petal margin*.—Entire.
*Petal number*.—5 or 6.
*Petal base*.—Truncate.
*Petal texture*.—Bullate, upper and under side.
*Color*.—Upper surface at first opening: Acidic: Blue 101B, 101C and 101D, all colors present. Basic: Red-Purple 73A through 73D, all colors present. Under surface at first opening: Acidic: Blue 101B, 101C and 101D, all colors present. Basic: Red-Purple 73A through 73D, all colors present. Upper surface at maturity: Acidic: Blue 101B, 101C and 101D, all colors present. Basic: Red-Purple 73A through 73D, all colors present. Under surface at maturity: Acidic: Blue 101B, 101C and 101D, all colors present. Basic: Red-Purple 73A through 73D, all colors present. Upper surface fading to: Acidic: Close to between Green 129A and Green 140B. Basic: Near RHS Violet 85CD. Lower surface fading to: Acidic: Near RHS Green 140C. Basic: Near RHS Violet 85CD.

Fertile flower sepal:
*Arrangement*.—Whorled.
*Number*.—5 to 7.
*Shape*.—Lanceolate.
*Tip*.—Obtuse.
*Base*.—Truncate.
*Margin*.—Entire.
*Length*.—1.5 mm.
*Width*.—0.5 mm.
*Texture, upper*.—Smooth, glabrous.
*Texture, lower*.—Sparsely scurfy.
*Color*.—Upper surface at first opening: Between RHS Yellow-Green 144B and 145D. Under surface at first opening: Between RHS Yellow-Green 144B and 145D. Upper surface at maturity: Near RHS Yellow-Green 144B. Under surface at maturity: Near RHS Yellow-Green 144B. Upper surface fading to: Near RHS Yellow-Green 144B. Lower surface fading to: Near RHS Yellow-Green 144B.

Fertile flower pedicel:
*Angle*.—Range of 15-40° from attachment.
*Strength*.—Moderate.
*Length*.—5.0 mm.
*Width*.—1.0 mm.
*Texture*.—Strigose.
*Color*.—Acidic: Near RHS Green 128B mixed with Blue-Green 111B. Basic: Red-Purple 73C and 73D.

Sterile flower sepal:
*Arrangement*.—Whorled, double whorled.
*Number*.—5 to 10.
*Shape*.—Wide deltate.
*Tip*.—Acute.
*Base*.—Truncate.
*Margin*.—Irregularly dentate and undulate.
*Length*.—Outer whorl 3.6 cm, inner whorl 2.5 cm.
*Width*.—Outer whorl 3.6 cm, inner whorl 2.2 cm.
*Texture, upper*.—Smooth, glabrous.
*Texture, lower*.—Smooth, glabrous.

*Color*.—Upper surface at first opening: Near RHS Green 142D. Upper surface at maturity: Near RHS Red-Purple 67C. Under surface at first opening: Near RHS Green 142D. Under surface at maturity: Near RHS Red-Purple 65B. Upper surface fading to: Near RHS Red-Purple 65B. Lower surface fading to: Near RHS Red-Purple 65C.

Sterile flower pedicel:

*Angle*.—About 70° from attachment.
*Strength*.—Moderately strong.
*Length*.—2.7 cm.
*Width*.—2 mm.
*Texture*.—Irregularly verrucate.
*Color*.—Near RHS Red-Purple 65A.

REPRODUCTIVE ORGANS

Sterile flower:

*Stamen number*.—9-12.
*Filament length*.—7.4 mm.
*Filament color*.—Acidic: Blue 101C. Basic. Purple 76B.
*Anther shape*.—Irregular ovate.
*Anther color*.—Acidic: Greyed-purple N187A. Basic: Purple 76B.
*Anther length*.—1 mm.
*Pollen quantity*.—Moderate.
*Gynoecium*.—Yes.
*Pistil number*.—2, 3 or 4.
*Pistil length*.—2 mm.
*Stigma shape*.—Elliptic.
*Stigma color*.—Acidic: Violet-Blue N95B. Basic: Red-Purple N74A.
*Style length*.—1.5 mm.
*Style color*.—Acidic: Blue 106B to Green group 132D. Basic: Red-Purple N74A.
*Ovary color*.—Near RHS Yellow-Green 144B.

Fertile flower:

*Stamen number*.—8 to 12.
*Filament length*.—13 mm.
*Filament color*.—Acidic: Blue 101B. Basic: Purple 76B.
*Anther shape*.—Oblong.
*Anther length*.—1.0 mm.
*Anther color*.—Acidic: Blue 106B. Basic: Purple 76B.
*Pollen amount*.—Abundant.
*Pollen color*.—Near RHS Yellow 2D.
*Pistil number*.—2 to 4.
*Pistil length*.—4.5 mm.
*Stigma shape*.—Irregular oblong.
*Stigma color*.—Acidic: Blue N95B. Basic: Red-Purple N74A.
*Style length*.—1.5 mm.
*Style color*.—Acidic: Blue 101B. Basic: Red-Purple N74A.
*Ovary color*.—Acidic: Blue 101D. Basic: Red-Purple N74A.

OTHER CHARACTERISTICS

Disease resistance: Neither resistance nor susceptibility to diseases or pests has been observed in this variety.
Cold tolerance: −25° C. to 37° C.
Fruit/seed production: Not observed.

What is claimed is:

1. A new and distinct cultivar of *Hydrangea* plant named 'SMNHSDD' as herein illustrated and described.

* * * * *